United States Patent [19]

Nakamura et al.

[11] Patent Number: 4,683,274
[45] Date of Patent: Jul. 28, 1987

[54] PROCESS FOR PRODUCING A WATER-ABSORBENT RESIN

[75] Inventors: Morio Nakamura, Kakogawa; Shigeji Obayashi, Akashi; Takushi Yamamoto, Himeji; Toshikazu Nakanishi, Kyoto; Hitoshi Tanaka; Yuji Sakamoto, both of Himeji, all of Japan

[73] Assignee: Seitetsu Kagaku Co., Ltd., Hyogo, Japan

[21] Appl. No.: 738,290

[22] Filed: May 28, 1985

[30] Foreign Application Priority Data

Oct. 5, 1984 [JP] Japan ................................. 59-210198

[51] Int. Cl.$^4$ .......................... C08F 20/04; C08F 2/32
[52] U.S. Cl. ................................... 526/216; 526/200; 526/204; 526/207; 525/317.1
[58] Field of Search .................... 526/200, 213, 216

[56] References Cited

U.S. PATENT DOCUMENTS 4,456,735  6/1984  Engelmann .................... 525/317
4,459,396  7/1984  Yamasaki ....................... 526/200

FOREIGN PATENT DOCUMENTS 2263256  10/1975  France .
 539898   2/1977  U.S.S.R. .

Primary Examiner—Christopher Henderson
Attorney, Agent, or Firm—Pollock, Vande Sande & Priddy

[57] ABSTRACT

A water-absorbent resin usable as a suitable water absorbent in sanitary materials and other fields can be produced by subjecting an aqueous solution of an $\alpha,\beta$-unsaturated carboxylic acid and of an alkali metal salt thereof to polymerization with a radical polymerization initiator in a petroleum-based hydrocarbon solvent in the presence or absence of a crosslinking agent and, in this polymerization, using a saccharose-fatty acid ester as a protective colloid agent.

10 Claims, No Drawings

PROCESS FOR PRODUCING A WATER-ABSORBENT RESIN

TECHNICAL FIELD

This invention relates to a process for producing a water-absorbent resin.

More particularly, the present invention relates to a process for producing a water-absorbent resin suitable for use particularly in the field of sanitary materials.

BACKGROUND ART

Water-absorbent resins have been used in the field of sanitation as menstrual articles, diaper, disposable house-cloth and the like, as well as in the field of agriculture and horticulture as water retentive materials and soil improvers. Further, they are useful in other various fields such as coagulation of sludges, prevention of dew condensation on construction materials, dehydration of oils and so on. They have been widely used particularly in the field of sanitation as menstrual articles, diaper, disposable house-cloth and the like. In this case, since they come in direct contact with human body, great importance has come to be placed on the safety of water absorbent-resins. In general, requirements for physical properties of water-absorbent resins include water absorbency, water absorption rate, gel strength after water absorption, shape and compatibility with other materials used together. Good water absorbent resins are those satisfying not only these physical properties but also safety.

As such water absorbent-resins, there are known high molecular resins which are crosslinked slightly, and their examples include crosslinked carboxymethyl cellulose, crosslinked polyethylene oxide, crosslinked hydrolyzate of starch-acrylonitrile graft copolymer, crosslinked polyacrylic acid salt and crosslinked vinyl alcohol-acrylic acid salt copolymer. Of these water-absorbent resins, crosslinked hydrolyzate of starch-acrylonitrile graft copolymer has a relatively high water absorbency. However, since it contains starch which is a natural high molecular substance and causes putrefactive decomposition, its storage over a long period of time is difficult. Moreover, its production process is complicated. With respect to crosslinked carboxymethyl cellulose and crosslinked polyethylene oxide, no product is available yet which has a satisfactory water absorbency. Crosslinked vinyl alcoholacrylic acid salt copolymer has a relatively high water absorbency. However, its production process is complicated incurring a high cost. In contrast, crosslinked acrylic acid salt polymer has a high water absorbency and can be prepared from a starting material, acrylic acid which is readily available commercially, can be produced at a uniform quality and inexpensively, and causes no putrefaction; thus, crosslinked acrylic acid salt polymer has many advantages and is said to be the most desirable water-absorbent resin.

As a process for polymerizing acrylic acid or an alkali metal acrylate, there are known bulk polymerization process, aqueous solution polymerization process, inverse emulsion polymerization process, inverse suspension polymerization process, etc. In processes other than inverse emulsion polymerization process and inverse suspension polymerization process, polymerization in an ordinary polymerization reactor is difficult because removal of the heat generated by polymerization is difficult and the polymerization mixture has an extremely high viscosity, and further it is difficult to obtain a product in powder state.

A process for producing a powdery polymer from an $\alpha,\beta$-unsaturated carboxylic acid in accordance with inverse emulsion polymerization process or inverse suspension polymerization process is known in Japanese Patent Publication No. 10644/1959, Japanese Patent Publication No. 30710/1979, Japanese Patent Application Kokai (Laid-Open) No. 26909/1981, etc. In order to carry out this process, selection of an appropriate protective colloid agent is necessary. This protective colloid agent is very important with regard to stabilization of W/O type suspension and control of the particle size of the polymer.

As said protective colloid agent, there are known sorbitan fatty acid esters (e.g. sorbitan monostearate and sorbitan monopalmitate), sorbitol fatty acid esters (e.g. sorbitol monostearate) and so forth. When inverse emulsion polymerization or inverse suspension polymerization is conducted using such a protective colloid agent, the polymer obtained becomes very fine powders having particle diameters as small as 100 to 10 $\mu$m. This necessitates setting up of a countermeasure for dust due to handling of the powders.

Such very fine powders are liable to form unswollen powder lumps when the powders absorb a liquid to be absorbed, resulting in insufficient absorption. Moreover, when this water-absorbent polymer is mixed with or attached to a pulverized pulp, a nonwoven cloth or the like, the polymer is liable to come off from the pulp or cloth.

When inverse suspension polymerization is conducted using a protective colloid agent having a HLB of 8 to 12 as described in Japanese Patent Application Kokai (Laid-Open) No. 131608/1981, such as sorbitan monolaurate, the polymer obtained becomes granular powders having particle diameters of 100 to 500 $\mu$m. This solves the above mentioned drawbacks; however, a large amount of the polymer adheres to the inside wall of a polymerization reactor during polymerization and it is not satisfactory in view of stable operation.

As other inverse suspension polymerization processes, there are known processes disclosed in Japanese Patent Application Kokai (Laid-Open) Nos. 158209/1982 and 158210/1982, etc. High molecular protective colloid agents used in these processes melt at the time of drying the formed polymer in an ordinary manner and induce partial or entire conversion of the polymer into lumps or adhesion of the polymer to the wall of a drier.

Protective colloid agents used in accordance with the processes described in Japanese Patent Application Kokai (Laid-Open) Nos. 98512/1982 and 98513/1982, etc. are not easily available commercially and the water-absorbent resins produced therewith are not sufficient in safety.

All the water-absorbent resin products obtained by the above mentioned processes have had a drawback that, when used in the field of sanitation, particularly in a diaper, even if such a water-absorbent resin is uniformly applied in the diaper, some of the resin powders that have absorbed a liquid to be absorbed tend to form lumps and the other cannot be effectively utilized.

SUMMARY OF INVENTION

The present inventors have made an extensive study on a process for stably producing a highly water-absorbent resin which is free from the above mentioned drawbacks of the conventional arts, has a large average particle diameter, is high in water absorbency and water absorption rate, has a sufficient gel strength and is excellent in safety. As a result, the present invention has been completed.

That is, the present inventors have investigated in detail on the production of a water-absorbent acrylic acid salt polymer based on the above mentioned inverse suspension polymerization process and as a result, have found that a highly water-absorbent resin having excellent characteristics as mentioned above can easily be obtained by using a succharose-fatty acid ester as a protective colloid agent. Based on this finding, the present invention has been completed.

DESCRIPTION OF THE PREFERRED EMBODIMENTS

The safety of a succharose-fatty acid ester used as a protective colloid agent in the present invention will be described in detail. A succharose-fatty acid ester, being an edible substance obtained from succharose and a fatty acid which are both natural products, is digested in human body and absorbed in the form of succharose and a fatty acid and accordingly can be added to foods in an unrestricted amount. Further, a succharose-fatty acid ester, having excellent biodegradation and safety, provides a protective colloid agent free from, in particular, environmental pollution and damage to human body. Furthermore, being unstimulating and protective to human eyes and skin, a succharose-fatty acid ester is most suitable for use in the field of sanitation as articles coming in frequent contact with human body such as diaper, menstrual articles, disposable house-cloth and the like.

The present invention provides a process for producing a water-absorbent resin wherein an aqueous solution of an $\alpha,\beta$-unsaturated carboxylic acid and of an alkali metal salt thereof is subjected to inverse suspension polymerization or inverse emulsion polymerization with a radical polymerization initiator in a petroleum-based hydrocarbon solvent in the presence or absence of a crosslinking agent, characterized by using a succharose-fatty acid ester as a protective colloid agent.

As the $\alpha,\beta$-unsaturated carboxylic acid used in the present invention, there can be cited acrylic acid and methacrylic acid. If necessary, a part of these acids can be replaced with other polymerizable carboxylic acid such as itaconic acid, crotonic acid, maleic acid, fumaric acid or the like.

As the alkali metal, there can be cited sodium, potassium, lithium, etc. In particular, sodium is preferable in view of safety because polysodium acrylate is approved as a food additive.

The aqueous solution of an $\alpha,\beta$-unsaturated carboxylic acid and of an alkali metal salt thereof is prepared by neutralizing an $\alpha,\beta$-unsaturated carboxylic acid with an alkali. In this case, the neutralization degree can vary widely and generally ranges from 40 to 100 mole %. When the neutralization degree is lower than 40 mole %, the crosslinking reaction of the monomers takes place to a very high extent, resulting in drastic reduction of water absorbency of the polymer formed as well as in increase of acidity of the polymer; and this is not desirable in utilization of the polymer. The monomer concentration in the aqueous solution of an $\alpha,\beta$-unsaturated carboxylic acid and of an alkali metal salt thereof is preferably from 30% by weight to their saturation solubility. When the concentration is lower than 30% by weight, yield per polymerization reactor is low, which is undesirable economically.

In the present process, polymerization can be conducted in the presence or absence of a crosslinking agent. A water-absorbent resin produced in the presence of a crosslinking agent has an improved gel strength but generally a reduced water absorbency. In contrast, a water-absorbent resin of self-crosslinking type produced in the absence of a crosslinking agent has a characteristic that the resin tends to have no reduced water absorbency for salts-containing aqueous solutions such as human urine, artificial urine and the like.

The polymerization process can appropriately be selected so as to best meet the application purpose of a water-absorbent resin produced, etc. As the crosslinking agent, if used, any crosslinking agent can be used as long as it can crosslink a polymer produced from an $\alpha,\beta$-unsaturated carboxylic acid monomer and its alkali metal salt monomer. As polymerizable crosslinking agents, there can be cited, for example, di- or tri(meth)acrylates of polyols such as ethylene glycol, propylene glycol, trimethylolpropane, glycerine, polyoxyethylene glycol, polyoxypropylene glycol, polyglycerine and the like; unsaturated polyesters obtained by reacting said polyols with unsaturated acids such as maleic acid, fumaric acid and the like; bisacrylamides such as N,N-methylenebisacrylamide and the like; di- or tri(meth)acrylates obtained by reacting a polyepoxide with (meth)acrylic acid; di-(meth)acryloyloxyethyl carbamates obtained by reacting a polyisocyanate such as tolylene diisocyanate, hexamethylene diisocyanate or the like with hydroxylethyl (meth)acrylate; allylated starch; allylated cellulose; diallyl phthalate; N,N',N''-triallylisocyanurate; divinylbenzene; etc.

Of these, there are ordinarily used ethylene glycol diacrylate, ethylene glycol dimethacrylate, diethylene glycol diacrylate, diethylene glycol dimethacrylate, propylene glycol diacrylate, propylene glycol dimethacrylate, polyethylene glycol diacrylate, polyethylene glycol dimethacrylate, diallyl phthalate, N,N',N''-triallylisocyanurate, N,N'-methylenebisacrylamide, etc.

As crosslinking agents which react with carboxyl groups present in the $\alpha,\beta$-unsaturated carboxylic acid and its alkali metal salt or their polymer, there are, for example, diglycidyl ether compounds, haloepoxy compounds and isocyanate compounds. Of these, diglycidyl ether compounds are particularly suitable. Specific examples of diglycidyl ether compounds include (poly)ethylene glycol diglycidyl ether, (poly)propylene glycol diglycidyl ether and (poly)glycerine diglycidyl ether. Of these, ethylene glycol diglycidyl ether gives the most preferable effect. Specific examples of haloepoxy compounds include epichlorohydrin, epibromohydrin and $\alpha$-methylepichlorohydrin. Specific examples of isocyanate compounds include 2,4-tolylenediisocyanate and hexamethylene diisocyanate. All of these crosslinking agents can be used in the present invention.

The crosslinking agent is generally used in an amount of 0.001 to 5% by weight, preferably 0.01 to 1% by weight. When it is used in an amount less than 0.001% by weight, the water-absorbent resin formed has a reduced gel strength after it has absorbed water, and the object of the present invention cannot be achieved. When the crosslinking agent is used in an amount more than 5% by weight, the water-absorbent resin formed has a remarkably reduced water absorbency, which is not desirable.

The petroleum-based hydrocarbon solvent used in the present invention is an aliphatic hydrocarbon, an alicyclic hydrocarbon or an aromatic hydrocarbon. Suitable aliphatic hydrocarbons are n-pentane, n-hexane, n-heptane, ligroin, etc. Suitable alicyclic hydrocarbons are cyclopentane, methylcyclopentane, cyclohexane, methylcyclohexane, etc. Suitable aromatic hydrocarbons are benzene, toluene, xylene, etc. Particularly, n-hexane, n-heptane, cyclohexane, benzene, toluene and xylene can be used advantageously because they are uniform in quality, easily available and inexpensive.

As the radical polymerization initiator, water-soluble radical polymerization initiators generally used, such as potassium persulfate, ammonium persulfate, sodium persulfate and the like are suitable. Also, redox initiators which comprise a combination of said initiators and a sulfite or the like may be used. When oil-soluble radical polymerization initiators are used, the polymer formed is generally water-soluble and accordingly these initiators need be used in the presence of a crosslinking agent. As the oil-soluble initiators, benzoyl peroxide, azobisisobutyronitrile, etc. are suitable. The radical polymerization initiator is suitably used in an amount of 0.005 to 1.0 mole % based on monomers. When it is used in an amount less than 0.005 mole %, a very long time is required for polymerization. When it is used in an amount more than 1.0 mole %, polymerization takes place suddenly and invites danger.

The protective colloid agent used in the inverse suspension polymerization or inverse emulsion polymerization of the present invention can be any saccharose-fatty acid ester. Preferably, the saccharose-fatty acid ester has a HLB of 2 to 16 because such an ester gives a good result. More particularly, the preferable saccharose-fatty acid ester is such that the fatty acid component is at least one member selected from stearic acid, palmitic acid, lauric acid and oleic acid and the number of ester groups per unit of saccharose is at least one selected from mono-, di- and tri-. Specific examples of such a saccharose-fatty acid ester include saccharose tristearate, saccharose di- and tristearates, saccharose mono-, di- and tristearates, saccharose distearate, saccharose mono- and distearates, saccharose monostearate and the like. In addition, at least one selected from mono-, di- and triesters of saccharose palmitate, saccharose laurate, saccharose oleate and the like can be used in the present invention.

When the saccharose-fatty acid ester has a HLB of 2 to 6, a bead-like polymer of 100 to 500 μm in particle diameter is obtained. When the ester has a HLB of 6 to 16, a granular polymer of 100 to 500 μm in particle diameter is obtained. When the saccharose-fatty acid ester of a HLB less than 2 is used, a stable emulsion can be formed but the polymer obtained tends to become lumps. When the saccharose-fatty acid ester having a HLB more than 16 is used, the ester is difficultly soluble in petroleum-based hydrocarbon solvents and accordingly cannot sufficiently act as a protective colloid agent. The protective colloid agent is suitably used in an amount of 0.05 to 15% by weight, preferably 0.1 to 10% by weight based on monomers. When it is used in an amount less than 0.05% by weight, a state of stable emulsion cannot be maintained. When it is used in an amount more than 15% by weight, no advantage corresponding to the increased amount can be obtained, which is uneconomical.

In inverse suspension or inverse emulsion polymerization, various protective colloids have hitherto been used but satisfactory results have not been obtained. In contrast, when the saccharose-fatty acid ester of the present invention is used, droplets of an aqueous solution of monomers are dispersed uniformly in a solvent; polymerization proceeds smoothly; and there is obtained a water-absorbent resin having large and uniform particle diameters. When this resin is used in sanitary articles such as diaper and the like, there is obtained an advantage that a liquid to be absorbed is uniformly absorbed throughout the entire area where the resin is applied. Further, the surface of this water-absorbent resin is coated with the above mentioned protective colloid. Owing to these reasons, the water-absorbent resin of the present invention exhibits various effects as shown in the following Examples.

The present invention will actually be explained below by way of Examples and Comparative Examples.

In the following Examples and Comparative Examples, water absorbency is a value obtained by the following procedure. That is, 1 g of a water-absorbent resin was dispersed in 200 ml of a 0.9% aqueous sodium chloride solution and allowed to swell sufficiently. After 2 hrs., the dispersion was filtered through a 100 mesh wire gauze. The weight of the swollen resin obtained was measured as the water absorbency of the resin.

Water absorption rate was defined as a time required for 1 g of a water-absorbent resin to absorb 30 ml of a 0.9% aqueous sodium chloride solution.

Gel strength was evaluated by hand-pressing a water-absorbent resin allowed to swell to a saturation point with a deionized water and was expressed according to the following criteria.

o: the swollen resin is not crushed even by strong pressing.

Δ: It is crushed by strong pressing.

x: It is readily crushed.

The results are shown in Table 1.

The performances of a water-absorbent resin when used in a diaper were evaluated as follows.

A pulverized pulp sheet weighing 100 g/m² was cut to a size of 40 cm × 10 cm. On one of these cut pulp sheets was uniformly dispersed 3 g of a water-absorbent resin. On this surface was superimposed another same pulp sheet. They were pressed by applying 1 kg/cm² of a pressure to their entire surfaces whereby an absorbent was formed.

One hundred and fifty ml of a 0.9% sodium chloride aqueous solution was poured around the center of the above prepared absorbent over 1 min and was allowed to stand for 10 min. Then, 20 sheets of filtering papers (Toyo Roshi No. 2) each cut to a size of 10 cm × 10 cm were placed around the center of the absorbent, and 3.5 kg of a weight having a bottom area of 10 cm × 10 cm was placed on the filtering papers for 3 min for weighting.

The amount of liquid absorbed by filtering papers was measured to obtain an amount of liquid recovered. The length over which the sodium chloride solution spread, was measured to obtain a diffusion length.

The results are shown in Table 1.

EXAMPLE 1

Two hundred and eighty ml of n-heptane was placed in a 500 ml, four-necked, round bottom flask provided with a stirrer, a reflux condenser, a dropping funnel and a nitrogen-blowing tube. Further, 0.75 g of saccharose stearate having a HLB of 5 which consists mainly of saccharose distearate (trade name: Ryoto Sugar Ester S-570 produced by Mitsubishi Kasei Shokuhin K. K.) was added and dispersed in n-heptane. Nitrogen gas was blown into the flask to remove oxygen dissolved in the dispersion. Then, the temperature of the dispersion was elevated to 50° C. to dissolve the protective colloid agent in n-heptane, after which the resulting solution was cooled to 30° C. Separately, in a 200 ml Erlenmeyer flask was placed 37.5 g of an aqueous solution containing 80% by weight of acrylic acid. With the flask being cooled from outside, 49.3 g of an aqueous solution containing 25.4% by weight of sodium hydroxide was added dropwise to neutralize acrylic acid by 75 mole %. Then, 0.045 g of potassium persulfate was added and dissolved. This aqueous solution of partially neutralized acrylic acid was added into the four-necked flask and dispersed therein. The flask inside was sufficiently purged again with nitrogen and the bath temperature was elevated to 55° to 65° C. The temperature was maintained for 1 hr to conduct polymerization. Water and n-heptane were distilled off and the residue was dried to obtain 40.5 g of a bead-like polymer having particle diameters of 150 to 350 μm. There was nothing adhering to the inside wall of the flask and the amount of the polymer which did not pass through a 20 mesh sieve was only 0.1 g.

EXAMPLE 2

The procedure of Example 1 was repeated except that the protective colloid agent was changed to saccharose stearate having a HLB of 2 which consists mainly of saccharose di- and tristearates (trade name: Ryoto Sugar Ester S-270 produced by Mitsubishi Kasei Shokuhin K. K.) and the amount of potassium persulfate was changed to 0.19 g, whereby 40.3 g of a bead-like polymer having particle diameters of 150 to 350 μm was obtained. There was nothing adhering to the inside wall of the flask and the amount of the polymer which did not pass through a 20 mesh sieve was 1.0 g.

EXAMPLE 3

The procedure of Example 1 was repeated except that the protective colloid agent was changed to saccharose stearate having a HLB of 9 which consists mainly of saccharose mono- and distearates (trade name: Ryoto Sugar Ester S-970 produced by Mitsubishi Kasei Shokuhin K. K.), whereby 40.3 g of a granular polymer having particle diameters of 150 to 300 μm was obtained. There was nothing adhering to the inside wall of the flask and the amount of the polymer which did not pass through a 20 mesh sieve was only 0.5 g.

EXAMPLE 4

The procedure of Example 1 was repeated except that the solvent was changed from n-heptane to toluene and the protective colloid agent was changed to saccharose palmitate having a HLB of 15 which consists mainly of saccharose monopalmitate (trade name: Ryoto Sugar Ester P-1570 produced by Mitsubishi Kasei Shokuhin K. K.), whereby 41.0 g of a granular polymer having particle diameters of 100 to 250 μm was obtained. There was nothing adhering to the inside wall of the flask and the amount of the polymer which did not pass through a 20 mesh sieve was 0.7 g.

EXAMPLE 5

The procedure of Example 1 was repeated except that 0.012 g of ethylene glycol dimethacrylate was added as a crosslinking agent, whereby 40.7 g of a bead-like polymer having particle diameters of 150 to 350 μm was obtained. There was nothing adhering to the inside wall of the flask and the amount of the polymer which did not pass through a 20 mesh sieve was only 0.2 g.

EXAMPLE 6

The procedure of Example 3 was repeated except that 0.019 g of N,N-methylenebisacrylamide was added as a crosslinking agent, whereby 40.8 g of a granular polymer having particle diameters of 150 to 300 μm was obtained. There was nothing adhering to the inside wall of the flask and the amount of the polymer which did not pass through a 20 mesh sieve was 0.6 g.

EXAMPLE 7

The procedure of Example 1 was repeated except that the protective colloid agent was changed to 2.25 g of saccharose stearate having a HLB of 3 which consists mainly of saccharose di- and tristearates (trade name: Ryoto Sugar Ester S-370 produced by Mitsubishi Kasei Shokuhin K. K.), whereby 41.5 g of a bead-like polymer having particle diameters of 200 to 400 μm was obtained. There was nothing adhering to the inside wall of the flask and the amount of the polymer which did not pass through a 20 mesh sieve was only 0.05 g.

EXAMPLE 8

Example 1 was repeated except that the solvent was changed from n-heptane to cyclohexane and 0.038 g of N,N-methylenebisacrylamide was added as a crosslinking agent, whereby 40.5 g of a bead-like polymer having particle diameters of 150 to 350 μm was obtained. There was nothing adhering to the inside wall of the flask and the amount of the polymer which did not pass through a 20 mesh sieve was only 0.2 g.

EXAMPLE 9

The procedure of Example 2 was repeated except that 0.019 g of ethylene glycol diglycidyl ether was added as a crosslinking agent, whereby 41.0 g of a bead-like polymer having particle diameters of 100 to 350 μm was obtained. There was nothing adhering to the inside wall of the flask and the amount of the polymer which did not pass through a 20 mesh sieve was 0.9 g.

EXAMPLE 10

The procedure of Example 1 was repeated except that 0.012 g of epichlorohydrin was added as a crosslinking agent, whereby 40.3 g of a bead-like polymer having particle diameters of 150 to 350 μm was obtained. There was nothing adhering to the inside wall of the flask and the amount of the polymer which did not pass through a 20 mesh sieve was only 0.1 g.

EXAMPLE 11

The procedure of Example 1 was repeated except that 0.038 g of hexamethylene diisocyanate was added as a crosslinking agent, whereby 40.5 g of a bead-like polymer having particle diameters of 150 to 350 μm was obtained. There was nothing adhering to the inside wall of the flask and the amount of the polymer which did not pass through a 20 mesh sieve was only 0.1 g.

EXAMPLE 12

The procedure of Example 5 was repeated except that the radical polymerization initiator was changed from potassium persulfate to 0.075 g of benzoyl peroxide, which was dissolved in the dispersing medium, whereby 40.5 g of a bead-like polymer having particle diameters of 150 to 350 μm was obtained. There was nothing adhering to the inside wall of the flask and the amount of the polymer which did not pass through a 20 mesh sieve was only 0.1 g.

EXAMPLE 13

The procedure of Example 12 was repeated except that the radical polymerization initiator was changed from benzoyl peroxide to azobisisobutyronitrile, whereby 40.8 g of a bead-like polymer having particle diameters of 150 to 350 μm was obtained. There was nothing adhering to the inside wall of the flask and the amount of the polymer which did not pass through a 20 mesh sieve was only 0.1 g.

EXAMPLE 14

The procedure of Example 13 was repeated except that the crosslinking agent was changed from ethylene glycol dimethacrylate to divinylbenzene, whereby 41.0 g of a bead-like polymer having particle diameters of 150 to 350 μm was obtained. There was nothing adhering to the inside wall of the flask and the amount of the polymer which did not pass through a 20 mesh sieve was only 0.1 g.

EXAMPLE 15

The procedure of Example 5 was repeated except that acrylic acid as a monomer was changed to methacrylic acid, whereby 40.9 g of a bead-like polymer having particle diameters of 100 to 300 μm was obtained. There was nothing adhering to the inside wall of the flask and the amount of the polymer which did not pass through a 20 mesh sieve was only 0.2 g.

EXAMPLE 16

The procedure of Example 5 was repeated except that 63.1 g of an aqueous solution containing 23.7% by weight of sodium hydroxide was added dropwise to neutralize by 90 mole %, whereby 41.5 g of a bead-like polymer having particle diameters of 200 to 350 μm was obtained. There was nothing adhering to the inside wall of the flask and the amount of the polymer which did not pass through a 20 mesh sieve was only 0.2 g.

EXAMPLE 17

The procedure of Example 1 was repeated except that 57.4 g of an aqueous solution containing 32.6% by weight of potassium hydroxide was added dropwise to neutralize by 80 mole %, whereby 45.1 g of a bead-like polymer having particle diameters of 150 to 350 μm was obtained. There was nothing adhering to the inside wall of the flask and the amount of the polymer which did not pass through a 20 mesh sieve was only 0.1 g.

EXAMPLE 18

The procedure of Example 1 was repeated except that 31.7 g of an aqueous solution containing 26.3% by weight of sodium hydroxide was added dropwise to neutralize by 50 mole %, whereby 36.5 g of a bead-like polymer having particle diameters of 150 to 350 μm was obtained. There was nothing adhering to the inside wall of the flask and the amount of the polymer which did not pass through a 20 mesh sieve was only 0.3 g.

EXAMPLE 19

The procedure of Example 7 was repeated except that the amount of potassium persulfate was changed to 0.11 g, whereby 40.9 g of a bead-like polymer having particle diameters of 200 to 400 μm was obtained. There was nothing adhering to the inside wall of the flask and the amount of the polymer which did not pass through a 20 mesh sieve was only 0.1 g.

COMPARATIVE EXAMPLE 1

The procedure of Example 1 was repeated except that the protective colloid agent was changed to 1.8 g of sorbitan monostearate, whereby 41.8 g of a bead-like polymer having particle diameters of 20 to 80 μm was obtained. There was nothing adhering to the inside wall of the flask and the amount of the polymer which did not pass through a 20 mesh sieve was only 0.3 g.

COMPARATIVE EXAMPLE 2

The procedure of Example 1 was repeated except that the protective colloid agent was changed to 0.56 g of sorbitan monolaurate and the amount of potassium persulfate was changed to 0.19 g, whereby 37.0 g of a granular polymer having particle diameters of 150 to 500 μm was obtained. The amount of the substance adhering to the inside wall of the flask was 2.0 g and the amount of the polymer which did not pass through a 20 mesh sieve was 1.5 g.

COMPARATIVE EXAMPLE 3

The procedure of Example 1 was repeated except that the protective colloid agent was changed to 1.8 g of ethyl cellulose (trade mark: ETHYL CELLULOSE N-200, manufactured by Hercules Co.), whereby 26.9 g of a bead-like polymer having particle diameters of 100 to 350 μm was obtained. The amount of the substance adhering to the inside wall of the flask was 8.1 g and the amount of the polymer which did not pass through a 20 mesh sieve was 6.5 g.

TABLE 1

|  | Water absorbency (g/g) | Water absorption rate (min) | Gel Strength | Diaper evaluation Amount of liquid recovered (g) | Diffusion length (cm) |
|---|---|---|---|---|---|
| Example 1 | 85 | 3 min 20 sec | Δ | 4.0 | 34 |
| Example 2 | 83 | 2 min 50 sec | Δ | 3.8 | 33 |
| Example 3 | 80 | 2 min 40 sec | Δ | 3.8 | 33 |
| Example 4 | 84 | 2 min | Δ | 4.0 | 32 |
| Example 5 | 73 | 1 min 50 sec | o | 1.5 | 32 |
| Example 6 | 70 | 1 min 20 sec | o | 1.4 | 32 |
| Example 7 | 83 | 1 min 30 sec | Δ | 3.6 | 34 |
| Example 8 | 60 | 55 sec | o | 2.1 | 31 |

TABLE 1-continued

| | Water absorbency (g/g) | Water absorption rate (min) | Gel Strength | Diaper evaluation | |
|---|---|---|---|---|---|
| | | | | Amount of liquid recovered (g) | Diffusion length (cm) |
| Example 9 | 72 | 1 min 40 sec | o | 1.4 | 32 |
| Example 10 | 70 | 1 min 30 sec | o | 1.4 | 32 |
| Example 11 | 68 | 1 min 15 sec | o | 1.3 | 32 |
| Example 12 | 75 | 1 min 55 sec | o | 1.5 | 32 |
| Example 13 | 77 | 2 min 10 sec | o | 2.0 | 33 |
| Example 14 | 73 | 2 min | o | 1.8 | 32 |
| Example 15 | 55 | 1 min | o | 3.5 | 30 |
| Example 16 | 80 | 2 min 20 sec | o | 1.6 | 34 |
| Example 17 | 79 | 2 min 40 sec | Δ | 3.8 | 33 |
| Example 18 | 60 | 52 sec | o | 3.4 | 30 |
| Example 19 | 65 | 1 min 20 sec | o | 1.3 | 33 |
| Comparative Example 1 | 46 | 65 min (unswollen powder lump) | o | 15.5 | 17 |
| Comparative Example 2 | 90 | 20 min (unswollen powder lump) | x | 9.5 | 21 |
| Comparative Example 3 | 75 | 17 min (unswollen powder lump) | Δ | 8.0 | 25 |

According to the present invention, there can be obtained a water-absorbent resin which has a high water absorbency and a high water absorption rate and accordingly can be used in such fields as sanitary materials, soil improvers and industrial applications. Since this water-absorbent resin has improved compatibility with materials such as pulp, has high safety toward human body and causes no environmental pollution, the resin is most suitable for use in a diaper.

Further, since the water-absorbent resin according to the present invention has larger particle diameters and need no countermeasure for dust, the resin can be used in wider applications than conventional water-absorbent resins.

Furthermore, in the present process, since no polymer adheres to the inside wall of a reactor, stable operation and accordingly economical and stable supply of a polymer product have become possible.

What is claimed is:

1. A process for producing a water-absorbent resin wherein an aqueous solution of an $\alpha,\beta$-unsaturated carboxylic acid and of an alkali metal salt thereof is subjected to polymerization with a radical polymerization initiator in a petroleum-based hydrocarbon solvent in the presence or absence of a crosslinking agent, characterized by using as a colloid agent, a saccharose-fatty acid ester having an HLB of 2 to 16 in an amount of 0.1 to 10% by weight based on the total of the $\alpha,\beta$-unsaturated carboxylic acid and the alkali metal salt thereof, the fatty acid component of the saccharose-fatty acid ester being at least one member selected from the group consisting of stearic acid, palmitic acid, lauric acid and oleic acid and the number of esters per unit of saccharose being at least one selected from mono-, di-, and tri-.

2. A process according to claim 1, wherein the $\alpha,\beta$-unsaturated carboxylic acid is acrylic acid.

3. A process according to claim 1, wherein the petroleum-based hydrocarbon solvent is one member or a mixture of at least two members selected from the group consisting of n-hexane, n-heptane, cyclohexane, benzene, toluene and xylene.

4. A process according to claim 3, wherein the petroleum-based hydrocarbon solvent is n-heptane.

5. A process according to claim 1, wherein the radical polymerization initiator is potassium persulfate.

6. A process according to claim 1, wherein the crosslinking agent is N,N-methylenebisacrylamide.

7. A process according to claim 1, wherein the crosslinking agent is ethylene glycol diglycidyl ether.

8. A process according to claim 1, wherein the saccharose-fatty acid ester consists mainly of saccharose distearate.

9. A process according to claim 1, wherein the saccharose-fatty acid ester consists mainly of saccharose di- and tristearates.

10. A process according to claim 1, wherein the saccharose-fatty acid ester consists mainly of saccharose mono- and distearates.

* * * * *